(12) United States Patent
Kahn

(10) Patent No.: US 7,012,167 B2
(45) Date of Patent: Mar. 14, 2006

(54) DIISOBUTYLENE PROCESS

(75) Inventor: Andrew P. Kahn, Eagleville, PA (US)

(73) Assignee: Lyondell Chemical Technology, L.P., Greenville, DE (US)

(*) Notice: Subject to any disclaimer, the term of this patent is extended or adjusted under 35 U.S.C. 154(b) by 222 days.

(21) Appl. No.: 10/681,395

(22) Filed: Oct. 8, 2003

(65) Prior Publication Data
US 2005/0080305 A1 Apr. 14, 2005

(51) Int. Cl.
C07C 1/00 (2006.01)
C07C 2/24 (2006.01)

(52) U.S. Cl. ............ 585/324; 585/329; 585/515; 585/526

(58) Field of Classification Search .......... 585/324, 585/326, 329, 510, 515, 526, 601
See application file for complete search history.

(56) References Cited

U.S. PATENT DOCUMENTS

| 3,351,635 A | 11/1967 | Kollar | 260/348.5 |
|---|---|---|---|
| 3,510,538 A | 5/1970 | Rosenthal | 260/682 |
| 4,100,220 A | 7/1978 | Bowman et al. | 260/683.15 |
| 4,155,945 A | 5/1979 | Levine | 585/639 |
| 4,165,343 A | 8/1979 | Levine et al. | 585/638 |
| 4,447,668 A | 5/1984 | Smith, Jr. et al. | 585/639 |
| 5,482,616 A * | 1/1996 | Brahma et al. | 208/143 |
| 5,625,109 A | 4/1997 | Gupta | 585/639 |
| 5,877,372 A | 3/1999 | Evans et al. | 585/510 |
| 5,998,685 A * | 12/1999 | Nierlich et al. | 585/329 |
| 6,376,731 B1 | 4/2002 | Evans et al. | 585/510 |

* cited by examiner

Primary Examiner—Walter D. Griffin
Assistant Examiner—In Suk Bullock
(74) Attorney, Agent, or Firm—Kevin M. Carroll

(57) ABSTRACT

This invention is a process for producing diisobutylene from isobutylene. The process comprises first oligomerizing isobutylene to diisobutylene using a sulfonic acid-type ion exchange resin. The oligomerization step is followed by contacting the diisobutylene product with an adsorbent to remove sulfur impurities produced during the oligomerization step. The adsorbent is a large pore zeolite such as zeolite X and zeolite Y. Optionally, the purified diisobutylene may be hydrogenated to isooctane using a hydrogenation catalyst.

9 Claims, No Drawings

DIISOBUTYLENE PROCESS

FIELD OF THE INVENTION

This invention relates to a process for producing diisobutylene from isobutylene. The process comprises first oligomerizing isobutylene to diisobutylene using a sulfonic acid-type ion exchange resin. The oligomerization step is followed by contacting the diisobutylene product with an adsorbent to remove sulfur impurities produced during oligomerization. The adsorbent is a large pore zeolite such as zeolite X or zeolite Y. The purified diisobutylene product may be optionally hydrogenated to isooctane using a hydrogenation catalyst.

BACKGROUND OF THE INVENTION

The oligomerization of olefins such as isobutylene using a sulfonic acid-type ion exchange resin catalyst is well-known in the art. For instance, U.S. Pat. No. 4,100,220 describes isobutylene oligomerization using a sulfonic acid resin catalyst and tertiary butanol selectivity enhancing modifier. In addition, U.S. Pat. No. 4,447,668 discloses isobutylene oligomerization using sulfonic acid resin catalyst A-15 with methyl t-butyl ether as solvent. Further, U.S. Pat. No. 5,877,372 describes the selective oligomerization of isobutylene using a sulfonic acid resin catalyst, tertiary butanol selectivity enhancing modifier and isooctane diluent. Lastly, U.S. Pat. No. 6,376,731 discloses the oligomerization of isobutylene in the presence of a $C_3$–$C_4$ alkane diluent to enhance oligomerization selectivity and tertiary butanol to promote selectivity to diisobutylene.

The diisobutylene product may be used as such or may be hydrogenated to isooctane as described in U.S. Pat. No. 5,877,372 and No. 6,376,731. Diisobutylene and isooctane are potential fuel blending compositions.

I have surprisingly found that the use of sulfonic acid-type ion exchange resin catalysts during the oligomerization step results in sulfur impurities in the diisobutylene product. Unfortunately, the presence of such sulfur impurities presents problems in regard to the use of the diisobutylene product. In the case of diisobutylene hydrogenation to form isooctane, the presence of sulfur impurities in diisobutylene results in deactivation of the hydrogenation catalyst. For diisobutylene product added directly to fuel streams, the presence of sulfur impurities is undesirable since combustion of fuel streams containing these impurities results in the release of sulfur oxides which are noxious, corrosive, and therefore, present a serious pollution problem. The United States Environmental Protection Agency has imposed increasingly more stringent requirements to reduce the amount of sulfur in fuel streams to mitigate this problem. It is desirable to develop a simplified procedure to produce diisobutylene containing a reduced amount of sulfur impurities.

In sum, new methods to produce diisobutylene by oligomerization of isobutylene over a sulfonic acid-type ion exchange resin catalyst are needed. Particularly needed are processes that result in lower sulfur impurities.

SUMMARY OF THE INVENTION

This invention is a process for producing diisobutylene. The process comprises a preliminary step of oligomerizing isobutylene over a sulfonic acid-type ion exchange resin catalyst to produce diisobutylene. The diisobutylene is then contacted with a large pore zeolite in order to remove sulfur impurities. Optionally, the purified diisobutylene product may be hydrogenated to isooctane in the presence of a hydrogenation catalyst. I have found that the use of an adsorbent results in lower sulfur impurities in the diisobutylene product. In addition, the use of an adsorbent prior to hydrogenation results in increased catalyst life of the hydrogenation catalyst in the optional hydrogenation step.

DETAILED DESCRIPTION OF THE INVENTION

The process of the invention comprises oligomerizing isobutylene over a sulfonic acid-type ion exchange resin catalyst to produce diisobutylene. Sulfonic acid resin catalysts are well known. Commercial examples of sulfonic acid resin catalysts include Amberlyst A-15, Purolite 275, Dowex 50 and the like. The oligomerization of isobutylene using sulfonic acid resin catalysts is well known in the art and has been described in U.S. Pat. Nos. 4,100,220, 4,447,668, 5,877,372, and 6,376,731, the teachings of which are hereby incorporated by reference.

The oligomerization of isobutylene typically is done by contacting the isobutylene feed with a sulfonic acid resin catalyst such as Amberlyst A-15 of Rohm & Haas, at oligomerization reaction conditions whereby exceedingly high reaction selectivity to the dimer is achieved. Generally small amounts of trimer are also formed in the oligomerization reaction. Usually, less than 10% of the converted isobutylene is converted into triisobutylene coproduct. In general, known oligomerization conditions can be employed in the oligomerization step. Suitable conditions include temperatures broadly in the range 0° C. to 200° C., preferably 10° C. to 100° C., and the use of pressures sufficient to maintain the liquid phase, illustratively above 50 psig, e.g. 50–500 psig.

The isobutylene feed may include any source of isobutylene, including raffinate streams and isobutylene from the dehydration of tertiary butanol as described in U.S. Pat. Nos. 5,625,109, 3,510,538, 4,165,343, and 4,155,945. The production of tertiary butyl alcohol by means of the Oxirane process is well known and widely practiced on an industrial scale. See, for example, U.S. Pat. No. 3,351,635.

During the oligomerization process, the isobutylene may be fed to the oligomerization reactor neat or in the presence of certain diluents. The presence of diluents is preferred. Tertiary butanol is preferably employed as a selectivity enhancing modifier. The use of tertiary butanol is taught in U.S. Pat. Nos. 4,100,220, 5,877,372, and 6,376,731. In addition, the use of a $C_3$–$C_{10}$ alkane diluent is preferred in order to further enhance reaction selectivity by reducing isobutylene feed concentration, and to aid in removal of the reaction exotherm. The use of alkane diluents is taught in U.S. Pat. No. 5,877,372 and No. 6,376,731.

The oligomerization product contains diisobutylene as well as some unreacted isobutylene and triisobutylene coproduct. It may be necessary to separate the diisobutylene from isobutylene using conventional procedures. If isobutylene is separated from the diisobutylene product, the isobutylene may be recycled back to the oligomerization reactor.

We have found that the diisobutylene product of oligomerization contains minor amounts of sulfur impurities from the sulfonic acid resin catalysts. These sulfur impurities are not desirable if the diisobutylene product is to be used as a fuel stream additive. In addition, when the diisobutylene is hydrogenated to isooctane, the sulfur impurities tend to slowly deteriorate the performance of the hydrogenation catalyst when used repeatedly or in a continuous process. Removal of the sulfur impurities is therefore an important aspect of the process of the invention.

This invention includes the removal of sulfur impurities from the diisobutylene product of oligomerization. Purification by solid-liquid extraction methods using adsorbents is well-known in the art. In a typical extraction, the diisobutylene is contacted in the liquid phase with at least one solid adsorbent. The adsorbents useful in the invention include large pore zeolites such as zeolite X or zeolite Y.

The large pore zeolites of the invention are useful for the removal of the sulfur impurities contained in the diisobutylene oligomerization product. The large pore zeolite used in the present invention are crystalline aluminosilicates having a pore size greater than about 6 Angstroms and preferably having an average pore size from about 6 Angstroms to about 15 Angstroms. Particularly preferred are zeolite X and zeolite Y. Preferably, the large pore zeolite is in the alkali metal (e.g., sodium) form rather than the acid form in order to provide effective impurities removal. Large pore zeolites are well known in the art.

The adsorptive contact is conveniently carried out at moderate temperatures, although temperature is not critical. Suitable temperatures are in the range of about 0° C. to 150° C., preferably 20° C. to 60° C. Flow rates of about 0.2 to 10 volumes of diisobutylene per volume of adsorbent per hour, preferably 1 to 5 are preferred.

The large pore zeolites retain the sulfur impurities adsorbed thereon resulting in diisobutylene having lower sulfur impurities. Initially, there can be substantially complete removal of the sulfur impurities and the recovered diisobutylene is of exceptional purity. Over the course of time the contact solids gradually become less effective for the removal of these components. Preferably, the extraction step removes at least 50 percent of the sulfur content from the diisobutylene product of oligomerization. More preferably, greater than about 70 percent of the sulfur content is removed during extraction. After extraction, the fuel stream is then separated and recovered using known techniques.

In accordance with the present invention at a pre-determined time when the separation efficiency has fallen below a desired point, the large pore zeolites are effectively regenerated, by contact with a heated vapor stream such as nitrogen or air at a temperature of at least 200° C. or by wash with a solvent such as methanol, acetone or water. It is advantageous to employ a plurality of parallel contact zones such that while one zone is being regenerated the feed is passed through a zone containing fresh or regenerated contact material so that optimum impurities removal can be achieved.

Following the extraction of sulfur impurities, and separating and recovering the diisobutylene having a reduced amount of sulfur impurities, the diisobutylene is optionally hydrogenated to isooctane. The hydrogenation step can be carried out using conventional methods. For example, the diisobutylene may be brought into contact with hydrogen in the liquid phase at moderate temperatures and pressures. Suitable reaction temperatures vary from 0° C. to 500° C., but preferably from 25° C. to 200° C. The reaction is preferably conducted at or above atmospheric pressure. The precise pressure is not critical. Typical pressures vary from 1 atmosphere to 100 atmospheres. Any suitable hydrogenation catalyst may be used, including but not limited to Raney nickel and supported nickel, palladium, and platinum catalysts. Suitable supports for nickel, palladium, and platinum include carbon, silica, alumina, diatomaceous earth, and the like. The hydrogenation may be performed in the presence or absence of a solvent. Following hydrogenation, the isooctane product can be recovered by removing the hydrogenation catalyst and the solvent (if present) in a conventional manner, to separate isooctane.

The hydrogenation reaction may be performed using any of the conventional reactor configurations known in the art for such hydrogenation processes. Continuous as well as batch procedures may be used. For example, the catalyst may be deployed in the form of a fixed bed or slurry.

The following examples merely illustrate the invention. Those skilled in the art will recognize many variations that are within the spirit of the invention and scope of the claims.

EXAMPLE 1

Extraction of Sulfur Impurities from Diisobutylene

Isobutylene is dimerized according to U.S. Pat. No. 5,877,372 at a temperature of 190° F. to produce a stream of 49.2 wt. % diisobutylene (DIB) and 1.5 wt. % triisobutylene (TIB) in isooctane. The product diisobutylene stream contains 700 ppb of sulfur.

Following the dimerization step, the diisobutylene product is passed over a variety of adsorbents, including Zeolite 13X (from Grace Davison), $Ni/SiO_2$ (Engelhard 3298E, reduced in H2 prior to use), MgO (from Martin Marietta), and alumina (Selexsorb COS and Selexsorb CL from Alcoa). In a typical experiment, 100 cc of the adsorbent is loaded in a tube (0.81 in ID) and the DIB feed stream is passed upflow at 150 cc/h. Samples of the stream are collected for S analysis using a Houston-Atlas Sulfur Analyzer.

The results are shown in Table 1. Surprisingly, only the large pore zeolite (Zeolite 13X) showed any ability to remove sulfur from the diisobutylene feed stream and was the only material to improve the performance of the hydrogenation catalyst.

EXAMPLE 2

Hydrogenation of Diisobutylene

Hydrogenation of a feed stream containing 49.2% diisobutylene (DIB), 1.5% triisobutylene (TIB) in isooctane is conducted in a plug flow reactor using $Ni/SiO_2$ catalyst (Engelhard 3298E, reduced in H2 prior to use, 30 cc, LHSV=5 $h^{-1}$, recycle/fresh=1 400 psig, 80° C.). The feed stream contains 700 ppb of sulfur, as analyzed using a Houston-Atlas Sulfur Analyzer. During the first 900 hours of operation, the DIB conversion declines from 99.9% to 98.7% while the TIB conversion declines from 100 to 68%. After 900 hours, a sulfur adsorbent bed is installed using 13X molecular sieve (100 cc). Analysis of the feed stream at the exit of the adsorbent reveals that the sulfur level is reduced to <50 ppb. As a result of the decrease in sulfur, the DIB conversion increased to 99.3% and remains steady while the TIB conversion increased to 80% and also remains steady. Deterioration in performance is observed only after 300 hours of operation, at which point the sulfur concentration at the exit of the adsorbent is >300 ppb. The adsorbent could be regenerated by calcining in air to 500° C. for 24 hours.

TABLE 1

Adsorption of S from Diisobutylene

| Run | Adsorbent | S after adsorption (ppb) | S Removal (%) |
|---|---|---|---|
| 1A | 13X | <50 | >93 |
| 1B * | Ni/SiO$_2$ | 700 | — |
| 1C * | MgO | 700 | — |
| 1D * | Alumina, Selexsorb COS | 700 | — |
| 1E * | Alumina, Selexsorb CL | 700 | — |

* Comparative Example

I claim:

1. A process comprising:
   (a) oligomerizing isobutylene in the presence of a sulfonic acid resin catalyst to produce a diisobutylene stream containing minor amounts of sulfur impurities; and
   (b) contacting the diisobutylene stream with a large pore zeolite to produce a diisobutylene product having a reduced amount of sulfur impurities.

2. The method of claim 1 wherein the large pore zeolite has an average pore size from about 6 Angstroms to about 15 Angstroms.

3. The method of claim 1 wherein the large pore zeolite is zeolite X.

4. The method of claim 1 wherein the large pore zeolite is zeolite Y.

5. The method of claim 1 wherein the large pore zeolite is in the sodium form.

6. The process of claim 1 comprising the additional step of (c) hydrogenating the diisobutylene product having a reduced amount of sulfur impurities in the presence of a hydrogenation catalyst to form isooctane.

7. The process of claim 6 wherein the hydrogenation catalyst is a supported nickel catalyst.

8. A process comprising:
   (a) oligomerizing isobutylene in the presence of a sulfonic acid resin catalyst to produce a diisobutylene stream containing minor amounts of sulfur impurities;
   (b) contacting the diisobutylene stream with a large pore zeolite selected from the group consisting of zeolite X and zeolite Y to produce a diisobutylene product having a reduced amount of sulfur impurities; and
   (c) hydrogenating the diisobutylene product having a reduced amount of sulfur impurities in the presence of a hydrogenation catalyst to form isooctane.

9. The process of claim 8 wherein the hydrogenation catalyst is a supported nickel catalyst.

* * * * *